US00PP34567P2

(12) United States Plant Patent
Catt

(10) Patent No.: US PP34,567 P2
(45) Date of Patent: Sep. 13, 2022

(54) ***HYDRANGEA* PLANT NAMED 'LISSJUDY'**

(50) Latin Name: *Hydrangea paniculata*
Varietal Denomination: LISSJUDY

(71) Applicant: Genesis Plant Marketing Ltd, Langford (GB)

(72) Inventor: Peter Catt, Liss (GB)

(73) Assignee: Genesis Plant Marketing Ltd, Langford (GB)

( * ) Notice: Subject to any disclaimer, the term of this patent is extended or adjusted under 35 U.S.C. 154(b) by 0 days.

(21) Appl. No.: 17/537,800

(22) Filed: Nov. 30, 2021

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

(56) References Cited

PUBLICATIONS

CPVO Application Consultation application No. 20193318 drawn to the *Hydrangea paniculata* plant named, 'LISSJUDY', Dec. 6, 2019, downloaded from https://online.plantvarieties.eu/publicConsultationDetails?registerId=20193318&denomination=LISSJUDY.*

* cited by examiner

*Primary Examiner* — Anne Marie Grunberg
(74) *Attorney, Agent, or Firm* — Weatherly IP Solutions, LLC; Barbara Campbell

(57) ABSTRACT

A new *Hydrangea* plant particularly distinguished by having a broad inverted triangular with a broad spreading upright habit, and white flowers with red-purple tinges at the apex, is disclosed.

3 Drawing Sheets

Genus and species: *Hydrangea paniculata.*
Variety denomination: 'LISSJUDY'.

BACKGROUND OF THE NEW PLANT

The present invention comprises a new and distinct variety of *Hydrangea* plant, botanically known as *Hydrangea paniculata*, and hereinafter referred to by the variety name 'LISSJUDY'. 'LISSJUDY' originated from an open pollination in England between two un- named *Hydrangea paniculata* parents. Seeds from the open-pollination were taken from the female parent and sown and a single plant was chosen in November 2009.

'LISSJUDY' was first propagated in July 2011 in The Netherlands. 'LISSJUDY' was found to reproduce true to type in successive generations of asexual propagation via softwood cuttings.

SUMMARY

The following are the most outstanding and distinguishing characteristics of this new variety when grown under normal horticultural practices in Boskoop, The Netherlands.

1. A broad inverted triangular shape with a broad spreading upright habit; and
2. White flowers with red-purple tinges at the apex.

DESCRIPTION OF THE PHOTOGRAPHS

This new *Hydrangea* plant is illustrated by the accompanying photographs which shows the plant's overall plant habit including form, and foliage. Photos were taken in August 2021 in Boskoop, The Netherlands. The colors shown are as true as can be reasonably obtained by conventional photographic procedures.

DESCRIPTION OF THE NEW VARIETY

Figure 1:
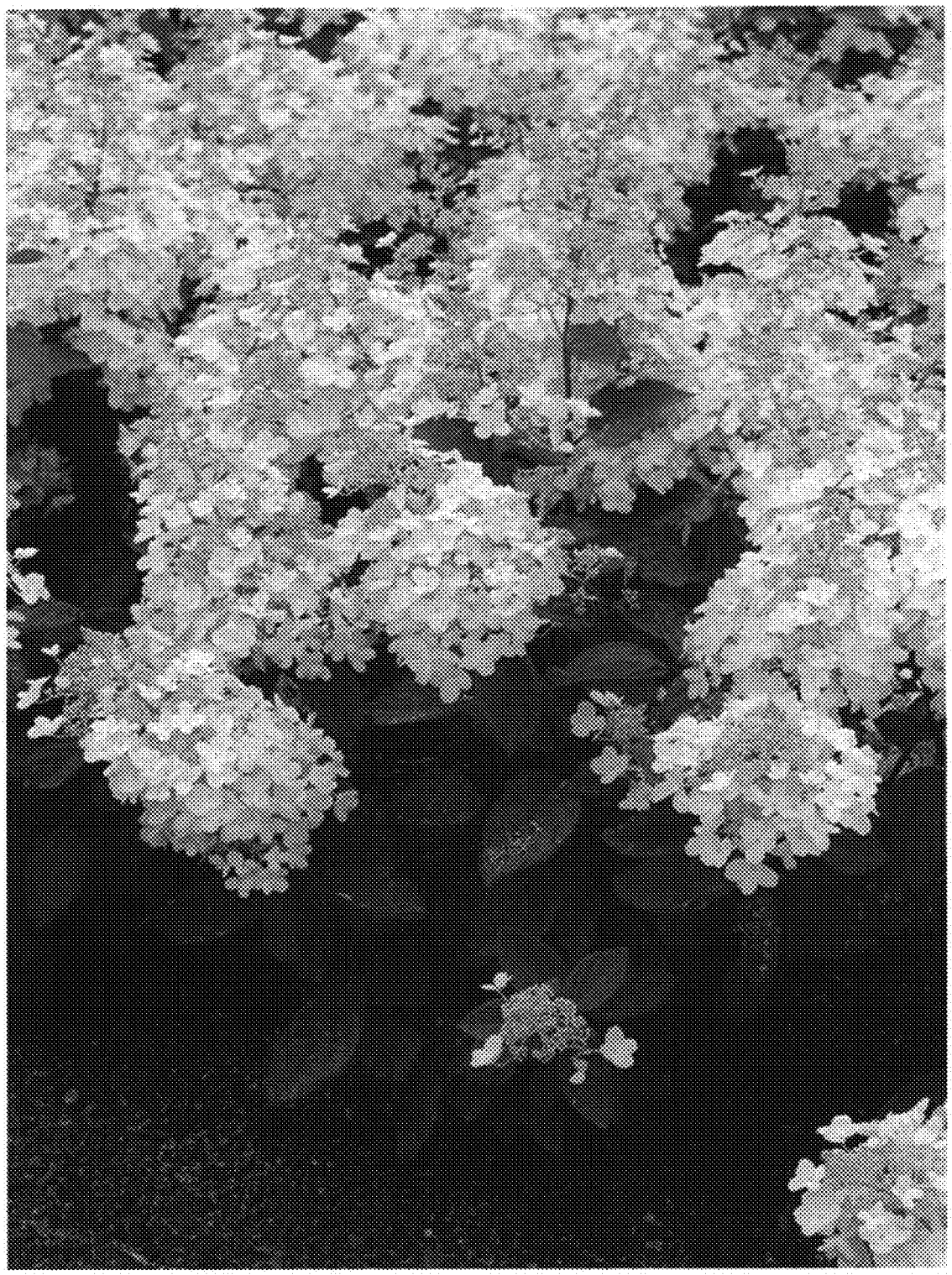
FIG. 1 shows the overall plant habit of 'LISSJUDY', including flowers, foliage, and buds.
Figure 2:
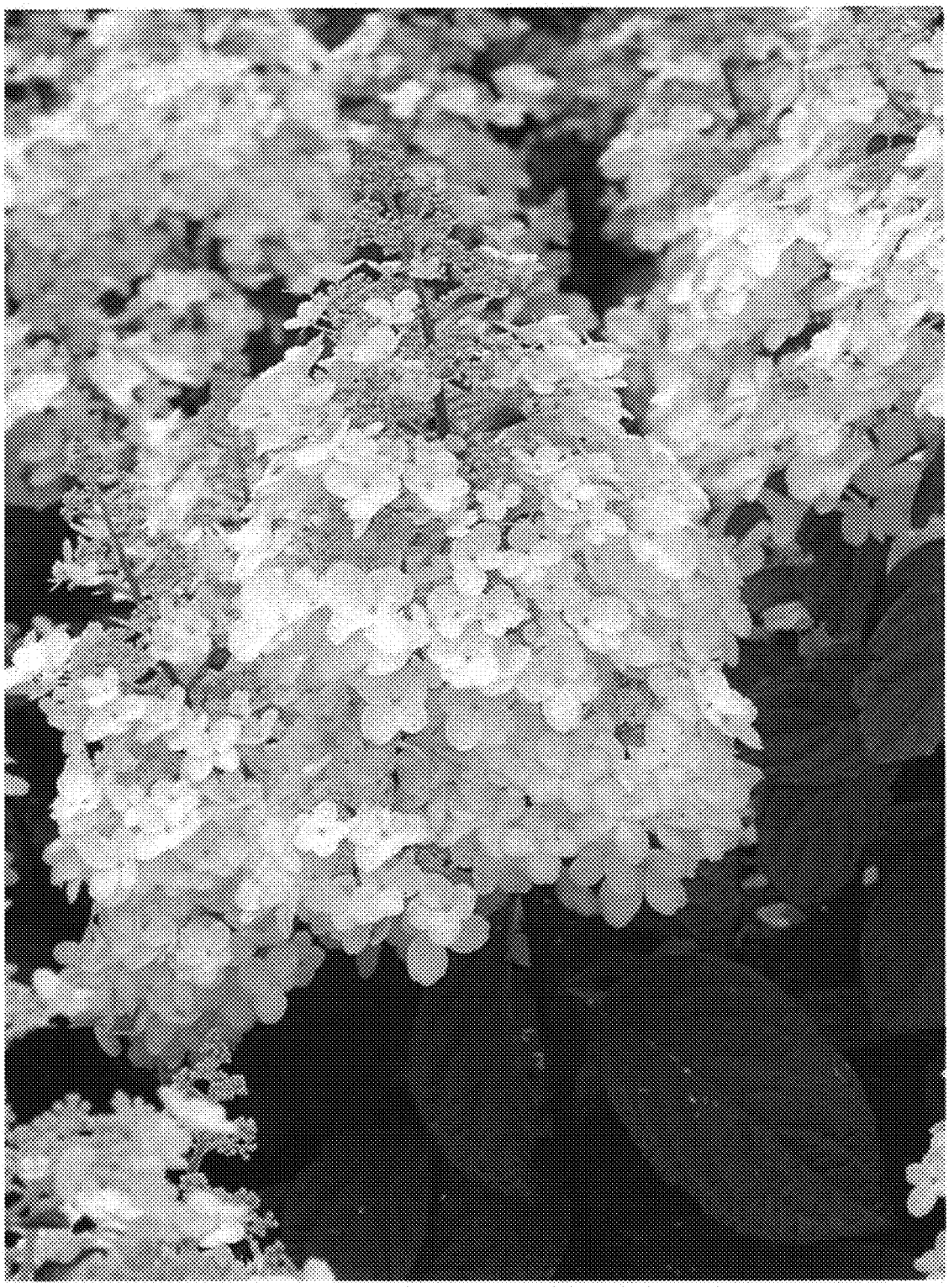
FIG. 2 shows a close-up of the flowers.
Figure 3:
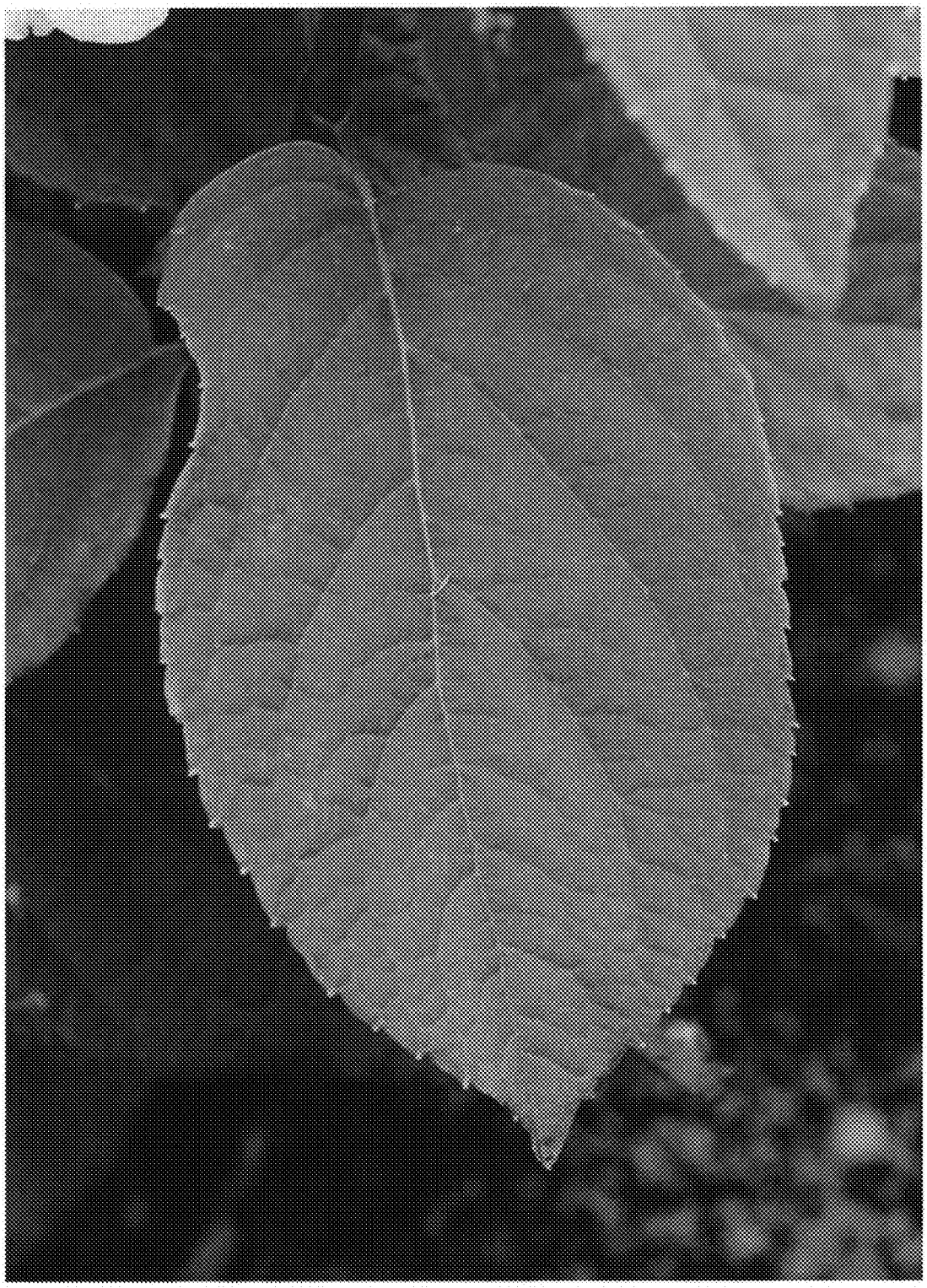
FIG. 3 shows a close-up of the foliage.

The following detailed descriptions set forth the distinctive characteristics of 'LISSJUDY'. The data which define these characteristics were collected from asexual reproductions carried out in Boskoop, The Netherlands. Data was collected on two-year old plants grown outdoors in a 19 cm circular pot The Netherlands in August 2021. The range of day temperatures was 16° C. to 26° C. and the range of night temperatures was 8° C. to 20° C. Color references are to The R.H.S. Colour Chart of The Royal Horticultural Society of London (R.H.S.), $6^{th}$ edition (2015).

Classification:
*Family.*—Hydrangeaceae.
*Botanical.*—*Hydrangea paniculata.*
*Common.*—*Hydrangea.*
*Designation.*—'LISSJUDY'.

Plant:
*Propagation type.*—Softwood.
*Time to produce a finished plant.*—Average is one year from propagation to a small finished plant.
*Plant shape.*—Broad inverted triangular.
*Growth habit.*—Broad spreading upright.
*Average plant height.*—78.1 cm.

*Average plant diameter.*—65.5 cm.

*Growth rate.*—Moderate.

*Vigor.*—Moderate.

*High temperature tolerance.*—At least tolerant to USDA Zone 9.

*Low temperature tolerance.*—At least tolerant to USDA Zone 5.

*Weather tolerances.*—Moderate tolerance to wind; moderate to high tolerance to rain.

*Disease/pest resistance and susceptibility.*—Not more susceptible to pests and diseases than other varieties of same species.

Branches:

*Habit.*—Freely branching.

*Basal branching.*—Present.

*Pinching.*—Not required but will improve branching.

*Lateral branches.*—Number of lateral branches per plant: Average of 12. Length: Average is 36.8 cm, excluding inflorescence. Diameter: Average is 0.7 cm. Internode length: Average is 7.5 cm. Appearance and shape: Rounded. Aspect/angle: Spreading-upright; average angle of 50 degrees to main branch. Strength: Strong.

*Color, immature.*—RHS 187C (Greyed-Purple).

*Color, mature.*—RHS N199A (Greyed-Brown) and RHS N199B (Greyed-Brown); older bar is RHS 197B (Greyed-Green), RHS 197C (Greyed-Green), RHS 199A (Greyed-Brown) and RHS 199B (Greyed-Brown).

*Pubescence.*—Young stems are sparsely covered with short adpressed hairs; length is 0.5 mm and white (hairs are too small and sparse to be accurately color with an R.H.S. designation).

*Lenticels.*—General: Stems are moderately covered with lenticels; lenticels are not visible on mature stems. Length: 1.5 mm. Width: 0.75 mm. Color: RHS 164B (Greyed-Orange) and RHS 164C (Greyed-Orange).

Foliage:

*Arrangement.*—Opposite or in whorls of 3.

*Number of leaves per lateral branch.*—Approximately 8.

*Shape.*—Ovate to elliptic.

*Apex.*—Apiculate to acute.

*Base.*—Short attenuate to near obtuse.

*Margin.*—Shallowly serrate.

*Length.*—Average is 12.7 cm.

*Width.*—Average is 7.6 cm.

*Texture.*—Upper surface: Smooth but sparsely pubescent with very short strigose hairs; length is 0.2 mm and colored greyed-white (hairs are too small to be accurately color with an R.H.S. designation). Lower surface: Smooth but moderately pubescent with very short adpressed hairs; length is 0.4 mm and colored greyed-white (hairs are too small to be accurately color with an R.H.S. designation).

*Venation pattern.*—Pinnate.

*Venation color.*—Upper surface: RHS 145A (Yellow-Green). Lower surface: Slightly lighter than RHS 146D (Yellow-Green).

*Color.*—Immature: Upper surface: RHS 144A (Yellow-Green). Lower surface: A blend of RHS 144B (Yellow-Green) and RHS 146C (Yellow-Green). Mature: Upper surface: RHS NN137A (Green). Lower surface: RHS 146B (Yellow-Green).

*Petiole.*—Length: Average is 1.9 cm. Diameter: Average is 3.0 mm. Color: Upper surface is a blend of RHS N186C (Greyed-Purple) and RHS 187A (Greyed-Purple) with RHS 174A and lower surface is RHS 151A (Yellow-Green) with RHS 187B (Greyed-Purple) and RHS 187A (Greyed-Purple) margins. Texture: Upper surface is slightly glossy and moderately covered with very short hairs that are about 0.4 mm in length and greyed-white in color (but too small to be measured with R.H.S. Color Chart); lower surface is slightly glossy and sparsely covered with very short hairs that are about 0.4 mm in length and greyed-white in color (but too small to be measured with R.H.S. Color Chart).

Flowers:

*Natural flowering season.*—Mid-summer to late summer.

*Time to produce a flowering plant.*—One season.

*Fragrance.*—Medium-strong, sweet and pleasant.

*General.*—Terminal panicle comprised of a center region of fertile florets surrounded by an outer ring of sterile florets; panicle is 28.6 cm in height and 18.5 cm in diameter and is irregular-conical in shape.

*Peduncle.*—Length: 26.8 cm. Diameter: 0.5 cm. Angle: For the main peduncle, 0 degrees; for lateral peduncles, 50 degrees to the main peduncle. Strength: Moderately strong. Texture: Densely covered with thick hairs; length of hairs is 0.5 mm and is matte RHS 156D (Greyed-White). Color: RHS 182B (Greyed-Red) and RHS 182C (Greyed-Red).

*Sterile florets.*—Bud: Length: 0.4 cm. Diameter: 1.2 cm. Shape: Broad cup-shaped. Color: RHS 10B. Florets: Aspect: Upright and outward to slightly drooping. Shape: Rotate. Diameter: 3.7 cm. Height: 0.9 cm. Lastingness on the plant: 6 weeks; flowers are persistent. Petals: Quantity per flower: Average of 4; occasionally 5. Arrangement: Rotate. Shape: Ovate. Apex: Acute. Base: Cuneate. Margin: Entire. Length: 3.0 mm. Width: 1.75 mm. Appearance and texture (both upper and lower surfaces): Matte and glabrous. Color: Upper surface: RHS NN155D (White) when opening and fully opened. Lower surface: RHS NN155A (White) and fading to RHS 58D (Red-Purple) towards the top when opening and RHS NN155A (White) when opening and fading to RHS 62C (Red-Purple) and RHS 62D (Red-Purple) when fully opened. Sepals: Quantity per flower: Average of 4; occasionally 5. Arrangement: Rotate. Shape: Broad elliptic to obovate. Apex: Shallowly retuse to obtuse. Base: Cuneate. Margin: Entire but occasionally shallowly toothed on upper half. Length: 2.0 cm. Width: 1.6 cm. Appearance and texture (both upper and lower surfaces): Matte and glabrous. Color: Upper surface: RHS 155C (White) when opening and RHS 155A (White) and tinged RHS 62A (Red-Purple) towards the margins and the top and fading to RHS 184D (Greyed-Purple). Lower surface: RHS 155C (White) when opening and RHS 155B (White) and tinged RHS 62A (Red-Purple) towards the margins and the top and fading to RHS 155A (White) to RHS 155B (White) and tinged with RHS 185C (Greyed-Purple) and RHS 185D (Greyed-Purple) towards the margins and the top. Pedicel: Length: 1.9 cm. Diameter: 1.0 mm. Angle: 40 degrees to the main peduncle. Strength:

Moderately strong. Appearance and texture: Matte and moderately covered with thin, adpressed hairs that are 0.4 mm in length and white (but too small to be accurately designated an R.H.S. color). Color: RHS NN155D (White).

*Fertile florets*.—Bud: Length: 4.0 mm. Diameter: 3.0 mm. Shape: Broad obovate. Color: RHS NN155A (White). Quantity per panicle: Approximately 750. Aspect: Upright. Shape: Rotate; petals dropped when maturing. Diameter: 9.0 mm. Depth (height): 6.0 mm. Lastingness on the plant: 5 days and flowers are persistent. Petals: Quantity of petals per flower: 5. Arrangement: Rotate. Shape: Ovate; moderately concave. Apex: Acute. Base: Cuneate. Margin: Entire. Length: 3.0 mm. Width: 1.5 mm. Appearance and texture (both upper and lower surfaces): Matte, smooth and glabrous. Color: Upper surface: RHS NN155D (White) when opening and fully opened. Lower surface: RHS NN155C (White) and the top is tinged with RHS 58D (Red-Purple) when opening and RHS NN155C (White) and the top is very slightly tinged with RHS 58D (Red-Purple) when fully opened. Sepals: Quantity per flower: 5. Arrangement: Rotate. Shape: Broad deltoid. Apex: Broad acuminate. Base: Broad cuneate. Margin: Entire. Length: 1.0 mm. Width: 1.2 mm. Appearance and texture (both upper and lower surfaces): Matte and glabrous. Color (both upper and lower surfaces): RHS 145C (Yellow-Green) when opening and fully opened. Length: 2.0 mm. Diameter: 0.5 mm. Angle: 20 degrees. Strength: Moderate. Pedicel: Texture and appearance: Moderately covered with thin pubescence; average length is 0.3 mm and colored green-white (hairs are too small to be accurately measured with RHS designation); matte. Color: RHS 157D (Green-White).

Reproductive organs:

*Androecium*.—Sterile flowers located on the androecium. Number of stamens per flower: 8. Filament length: 3.0 mm. Filament color: RHS NN155D (White). Anther shape: Broad oblong. Anther length: 0.75 mm. Anther color: RHS 157A (Green-White). Pollen quantity: Low to moderate. Pollen color: RHS 156D (Greyed-White).

*Gynoecium*.—Fertile flowers located on the androecium. Quantity of stamen per flower: 10. Filament length: 5.0 mm. Filament color: RHS NN155D (White). Anther shape: Broad oblong. Anther length: 0.75 mm. Anther color: RHS 157A (Green-White). Pollen quantity: Low to moderate. Pollen color: RHS 156D (Greyed-White). Quantity of pistils per flower: 3. Pistil length: 2.0 mm. Stigma shape: Club-shaped. Stigma color: RHS 157D (Green-White). Style length: 1.0 mm. Style color: RHS 145D (Yellow-Green). Ovary color: RHS 145D (Yellow-Green).

*Seed*.—Not observed to date.

COMPARISON WITH COMMERCIAL VARIETY

No comparison can be made with both parents of 'LISSJUDY' as the parents are unknown and un-named.

'LISSJUDY' can be distinguished between the commercial variety 'Limelight' (U.S. Plant Pat. No. 12,874) in Table 1.

TABLE 1

Comparison with Commercial Variety

| Characteristic | 'LISSJUDY' | 'Limelight' |
|---|---|---|
| Height of plant | 78.1 cm | 180 cm to 240 cm |

I claim:

1. A new and distinct variety of *Hydrangea* plant designated 'LISSJUDY' as illustrated and described herein.

* * * * *